United States Patent
Chen

(10) Patent No.: US 10,994,146 B2
(45) Date of Patent: May 4, 2021

(54) EXTERNAL DEVICE WITH ELECTROMAGNET FOR USE WITH AN IMPLANTABLE MEDICAL DEVICE

(71) Applicant: Boston Scientific Neuromodulation Corporation, Valencia, CA (US)

(72) Inventor: Joey Chen, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 170 days.

(21) Appl. No.: 16/162,940

(22) Filed: Oct. 17, 2018

(65) Prior Publication Data

US 2019/0175925 A1  Jun. 13, 2019

Related U.S. Application Data

(60) Provisional application No. 62/597,725, filed on Dec. 12, 2017.

(51) Int. Cl.
  *A61N 1/372* (2006.01)
  *A61N 1/375* (2006.01)
  *A61N 1/378* (2006.01)

(52) U.S. Cl.
  CPC ......... *A61N 1/37217* (2013.01); *A61N 1/375* (2013.01); *A61N 1/3787* (2013.01); *A61N 1/37247* (2013.01)

(58) Field of Classification Search
  CPC .. A61N 1/37217; A61N 1/3787; A61N 1/275; A61N 1/37247; A61N 1/37223; A61N 1/37211
  USPC ................................................ 607/30–32, 60
  See application file for complete search history.

(56) References Cited

U.S. PATENT DOCUMENTS

| | | | |
|---|---|---|---|
| 6,516,227 B1 | 2/2003 | Meadows et al. | |
| 7,167,756 B1 | 1/2007 | Torgerson | |
| 7,496,404 B2 | 2/2009 | Meadows et al. | |
| 8,335,569 B2 | 12/2012 | Aghassian | |
| 8,473,070 B2 * | 6/2013 | Marnfeldt | A61N 1/378 607/63 |
| 8,498,716 B2 | 7/2013 | Chen et al. | |
| 8,768,453 B2 | 7/2014 | Parramon et al. | |
| 2009/0018599 A1 * | 1/2009 | Hastings | A61N 1/37512 607/32 |
| 2012/0035687 A1 | 2/2012 | Lu et al. | |
| 2012/0262108 A1 * | 10/2012 | Olson | H02J 7/025 320/108 |
| 2014/0350635 A1 * | 11/2014 | Strother | A61N 1/36067 607/45 |
| 2015/0080982 A1 * | 3/2015 | Van Funderburk | A61N 1/37247 607/59 |

\* cited by examiner

*Primary Examiner* — Carl H Layno
*Assistant Examiner* — Anh-Khoa N Dinh
(74) *Attorney, Agent, or Firm* — Lewis & Reese, PLLC

(57) ABSTRACT

An external device for use with an implantable medical device includes circuitry that is configured to drive a coil to produce a static electromagnetic field to change a status of the implantable medical device. The static electromagnetic field may replace a physical magnet, which may not be commonly carried by a patient, to induce an emergency shutdown of the implantable medical device. The external device may be a charger or controller that is used to charge or communicate with the implantable medical device, and the coil may primarily be used for those charging and telemetry functions in such devices.

20 Claims, 5 Drawing Sheets

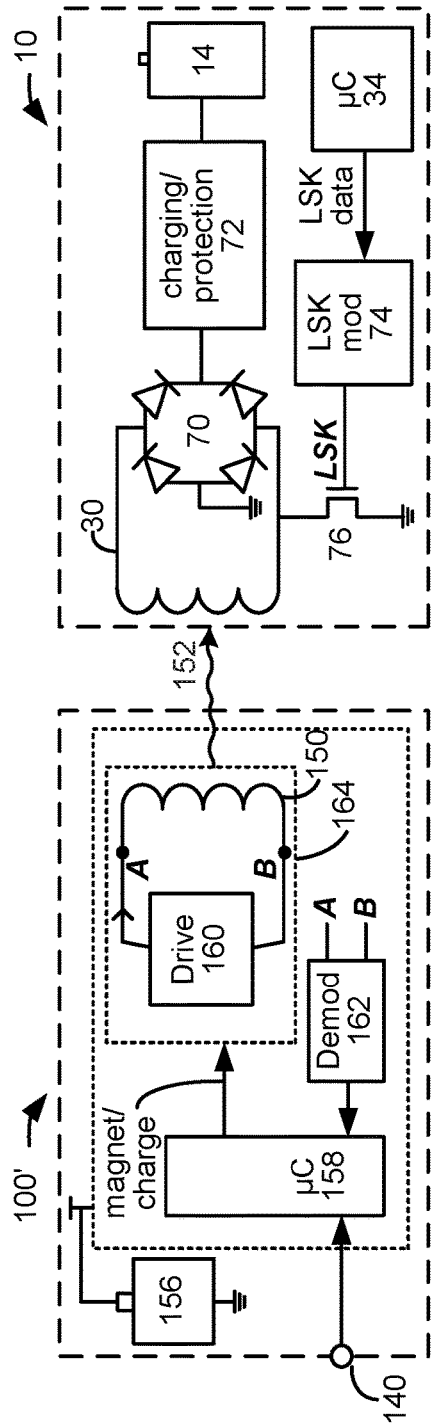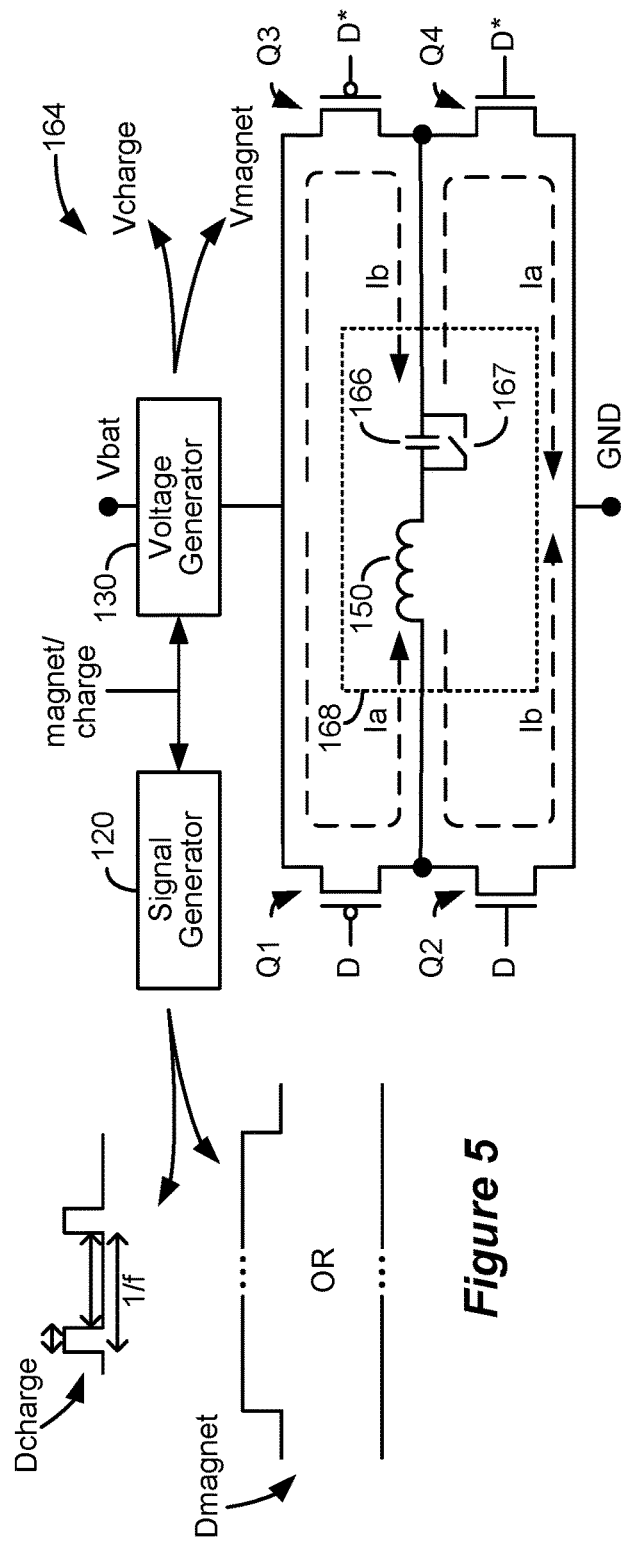
Figure 4
Figure 5

EXTERNAL DEVICE WITH ELECTROMAGNET FOR USE WITH AN IMPLANTABLE MEDICAL DEVICE

CROSS REFERENCE TO RELATED APPLICATIONS

This is a non-provisional application of U.S. Provisional Patent Application Ser. No. 62/597,725, filed Dec. 12, 2017, which is incorporated by reference, and to which priority is claimed.

FIELD OF THE TECHNOLOGY

The present application relates to external devices that are configured for use with an implantable medical device.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the disclosed aspects within a Spinal Cord Stimulation (SCS) system, such as that disclosed in U.S. Pat. No. 6,516,227. However, the present disclosure may find applicability with any Implantable Medical Device (IMD) or in any IMD system.

As shown in FIG. 1, a traditional SCS system includes an IMD 10, which includes a biocompatible device case 12 that is formed from a metallic material such as titanium. The case 12 typically comprises two components that are welded together, and it holds the circuitry and battery 14 (FIG. 2) necessary for the IMD 10 to function, which battery 14 may be either rechargeable or primary (non-rechargeable) in nature. The IMD 10 is coupled to electrodes 16 via one or more electrode leads 18 (two of which are shown). The proximal ends of the leads 18 include electrode terminals 20 that are coupled to the IMD 10 at one or more connector blocks 22 fixed in a header 24, which can comprise an epoxy for example. Contacts in the connector blocks 22 make electrical contact with the electrode terminals 20, and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, there are sixteen electrodes 16 split between two leads 18, although the number of leads and electrodes is application specific and therefore can vary. In a traditional SCS application, two electrode leads 18 are typically implanted with one on each of the right and left sides of the dura within the patient's spinal column.

As shown in FIG. 2, IMD 10 contains a charging coil 30 for wireless charging of the IMD's battery 14 using an external charging device 100, assuming that battery 14 is a rechargeable battery. If IMD 10 has a primary battery 14, charging coil 30 in the IMD 10 and external charger 100 can be eliminated. IMD 10 also contains a telemetry coil antenna 32 for wirelessly communicating data with an external controller device 200, which is explained further below. In other examples, antenna 32 can comprise a short-range RF antenna such as a slot, patch, or wire antenna. IMD 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IMD 10, in plan and cross section views. External controller 200 may be used to control and monitor the IMD 10 via a bidirectional wireless communication link 252 passing through a patient's tissue 5. For example, the external controller 200 may be used to provide or adjust a stimulation program for the IMD 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 252 can occur via magnetic inductive coupling between a coil antenna 250 in the external controller 200 and the IMD 10's telemetry coil 32 as is well known. Typically, the magnetic field comprising link 252 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 252 need not be by magnetic induction, and may comprise short-range RF telemetry (e.g., Bluetooth, WiFi, Zigbee, MICS, etc.) if antennas 250 and 32 and their associated communication circuitry are so configured. The external controller 200 is generally similar to a cell phone and includes a hand-held, portable housing.

External charger 100 provides power to recharge the IMD's battery 14 should that battery be rechargeable. Such power transfer occurs by energizing a charging coil 150 in the external charger 100, which produces a magnetic field comprising transcutaneous link 152, which may occur with a different frequency (f2=80 kHz) than data communications on link 252. This magnetic field 152 energizes the charging coil 30 in the IMD 10, which is rectified, filtered, and used to recharge the battery 14. Link 152, like link 252, can be bidirectional to allow the IMD 10 to report status information back to the external charger 100, such as by using Load Shift Keying as is well-known. For example, once circuitry in the IMD 10 detects that the battery 14 is fully charged, it can cause charging coil 30 to signal that fact back to the external charger 100 so that charging can cease. Like the external controller 200, external charger 100 generally comprises a hand-holdable and portable housing.

External controller 200 and external charger 100 are described in further detail in U.S. Patent Application Publication 2015/0080982. Note also that the external controller 200 and external charger 100 can be partially or fully integrated into a single external system, such as disclosed in U.S. Pat. Nos. 8,335,569 and 8,498,716.

SUMMARY

An external device for use with an implantable medical device is disclosed, comprising a coil; and circuitry that is configured to produce a direct current through the coil in a first mode of operation to generate a static magnetic field to change a status of the implantable medical device. The static magnetic field may be configured to cause one or more components in the implantable medical device to be disconnected from a battery in the implantable medical device.

The external device may be an external charger, and the circuitry may be configured to produce an alternating current through the coil in a second mode of operation. The alternating current may produce an alternating magnetic field to charge a battery in the implantable medical device.

The external device may be an external controller, and the circuitry may be configured to produce an alternating current through the coil in a second mode of operation. The circuitry may be configured to communicate data to the implantable medical device using a frequency of the alternating current.

The circuitry may include a signal generator that generates a signal to control a conductive path through the coil. The circuitry may include an H-bridge and the signal may control a plurality of switches in the H-bridge. The signal may be a constant signal in the first mode of operation. The signal may be a square wave signal in a second mode of operation, and the square wave signal may produce an alternating current through the coil. The circuitry may be configured to adjust a duty cycle of the square wave signal to control a strength of an alternating magnetic field that is produced by the alternating current through the coil.

A system is disclosed, comprising an implantable medical device; and an external device, comprising a coil; and circuitry that is configured to produce a direct current through the coil in a first mode of operation to generate a static magnetic field to change a status of the implantable medical device. The implantable medical device may include a magnet sensor to detect the static magnetic field, and the magnet sensor may be a reed switch or a Hall effect sensor. The implantable medical device may further include a signal conditioning circuit that receives a signal from the magnet sensor. The implantable medical device may further include circuitry that is configured to disconnect one or more components in the implantable medical device from a battery in the implantable medical device when the magnet sensor detects the static magnetic field.

The external device may be an external charger, and the circuitry may be configured to produce an alternating current through the coil in a second mode of operation. The alternating current may produce an alternating magnetic field to charge a battery in the implantable medical device.

The external device may be an external controller, and the circuitry may be configured to produce an alternating current through the coil in a second mode of operation. The circuitry may be configured to communicate data to the implantable medical device using a frequency of the alternating current.

The circuitry may include a signal generator that generates a signal to control a conductive path through the coil. The circuitry may include an H-bridge and the signal may control a plurality of switches in the H-bridge. The signal may be a constant signal in the first mode of operation. The signal may be a square wave signal in a second mode of operation, and the square wave signal may produce an alternating current through the coil. The circuitry may be configured to adjust a duty cycle of the square wave signal to control a strength of an alternating magnetic field that is produced by the alternating current through the coil.

A non-transitory computer-readable medium is disclosed having instructions stored thereon to cause control circuitry to produce a direct current through a coil in an external device in a first mode of operation to generate a static magnetic field to change a status of an implantable medical device.

BRIEF DESCRIPTION OF THE DRAWINGS

FIG. 4 is a block diagram showing circuitry in a modified external charger and an IMD in accordance with aspects of the disclosure.

FIG. 5 shows components of example charging circuitry in the modified external charger in accordance with aspects of the disclosure.

DETAILED DESCRIPTION

Figure 3:
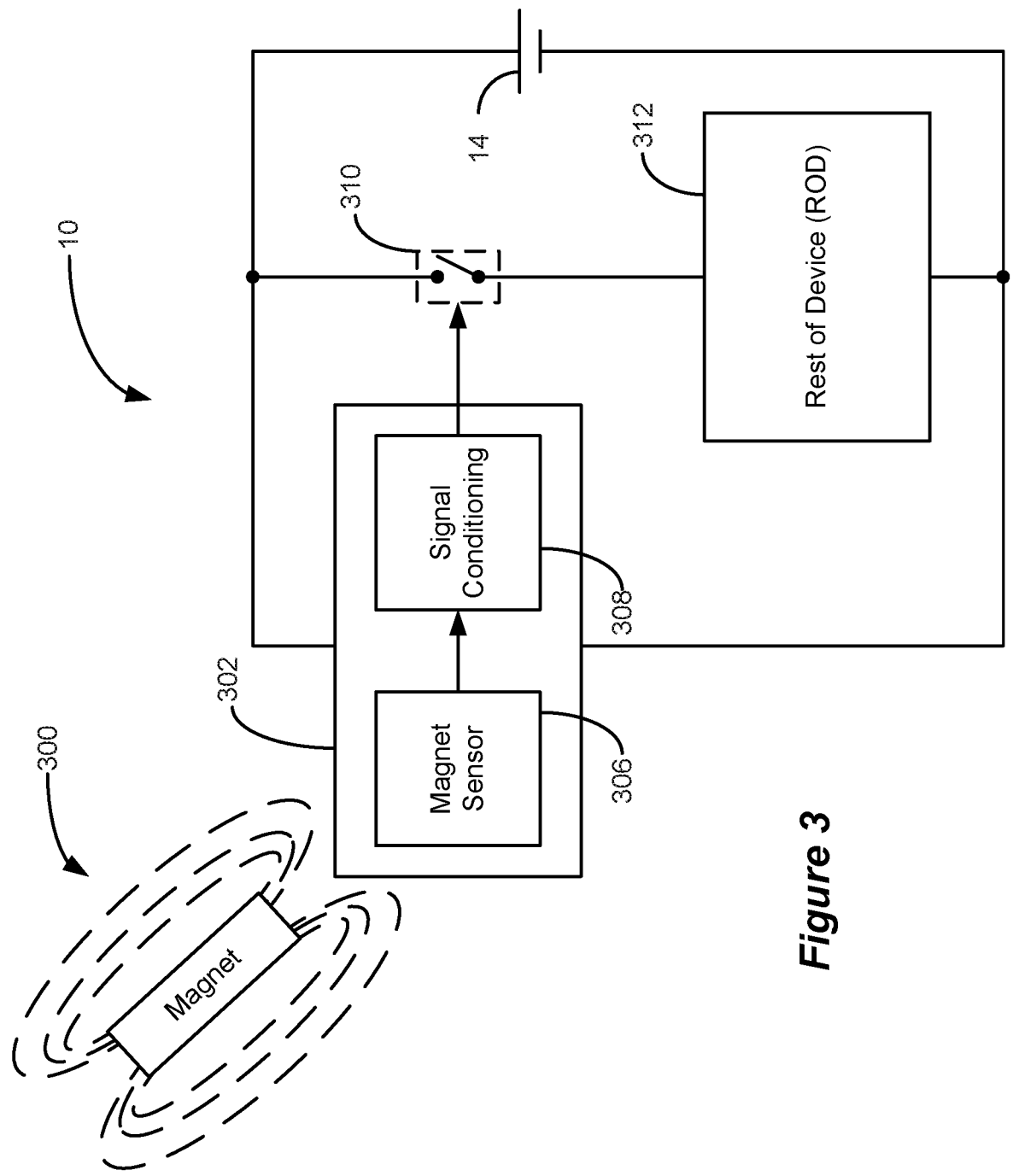
FIG. 3 shows a magnet and magnetic sensing circuitry in an IMD for initiating an emergency shutdown of the IMD in accordance with aspects of the disclosure.

IMD 10 can comprise circuitry that enables a user or a clinician to shutdown the IMD 10 in case of emergencies. Such emergencies can arise when the IMD 10 malfunctions, undesirably over-stimulates the patient, does not provide stimulation at all, etc. FIG. 3 shows circuitry 302 that may be used in the IMD 10 for emergency shutdown. A user or clinician brings a magnet 300 (such as a bar magnet) near the location on the patient's body where the IMD 10 is situated. A magnet sensor 306, such as a reed switch or omnidirectional Hall effect sensor, detects the presence of magnet 300 by way of sensing its magnetic field, and sends an electrical signal (voltage or current) to a signal conditioning circuit 308. The signal conditioning circuit 308 suppresses any stray and transient signals (e.g., reed bounce) received from the magnet sensor 306. Once a sufficient signal indicating presence of magnet 300 is detected, the signal conditioning circuit 308 outputs a signal that opens switch 310. Once switch 310 is open, Rest of the Device (ROD) 312 will be disconnected from battery 14. ROD 312 will typically include all the circuitry responsible for the functioning of the IMD 10. For example, ROD 312 can include the microprocessor, charging circuits, telemetry circuits, stimulation circuits, volatile and non-volatile memory, etc. Upon being disconnected from the battery 14, these circuits will cease to function.

One drawback of this emergency shutdown technique is that because it is so rarely used, the user may not normally carry the magnet 300 with them and therefore may not have the magnet 300 when it is needed. The inventor has determined that external devices that are more commonly carried by the user, such as the controller 200 and charger 100, can be modified to generate an electromagnet that performs the same functionality as the magnet 300.

Figure 1:
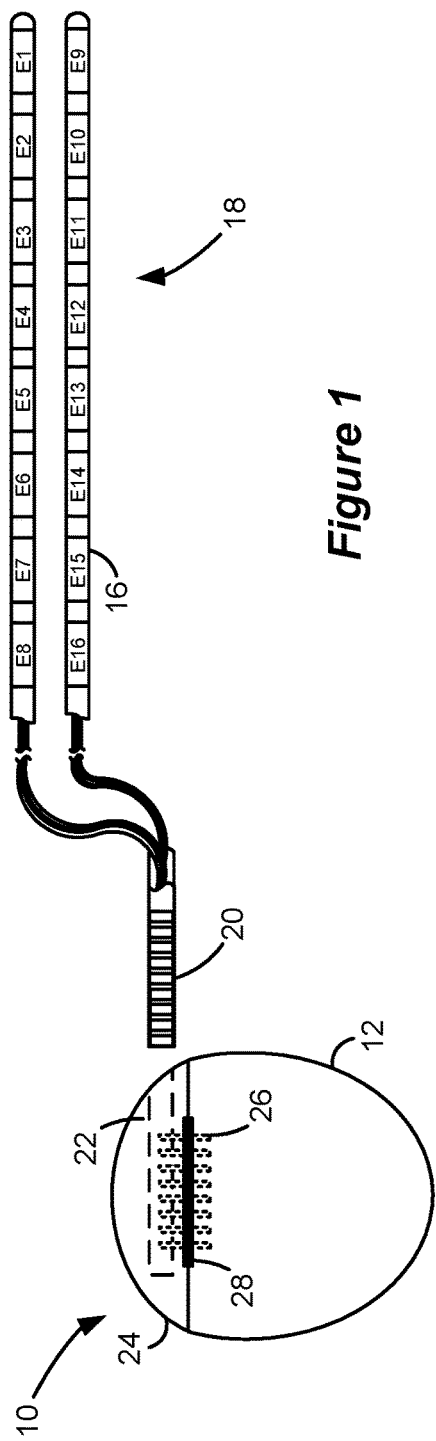
FIG. 1 shows an implantable medical device (IMD).
Figure 2:
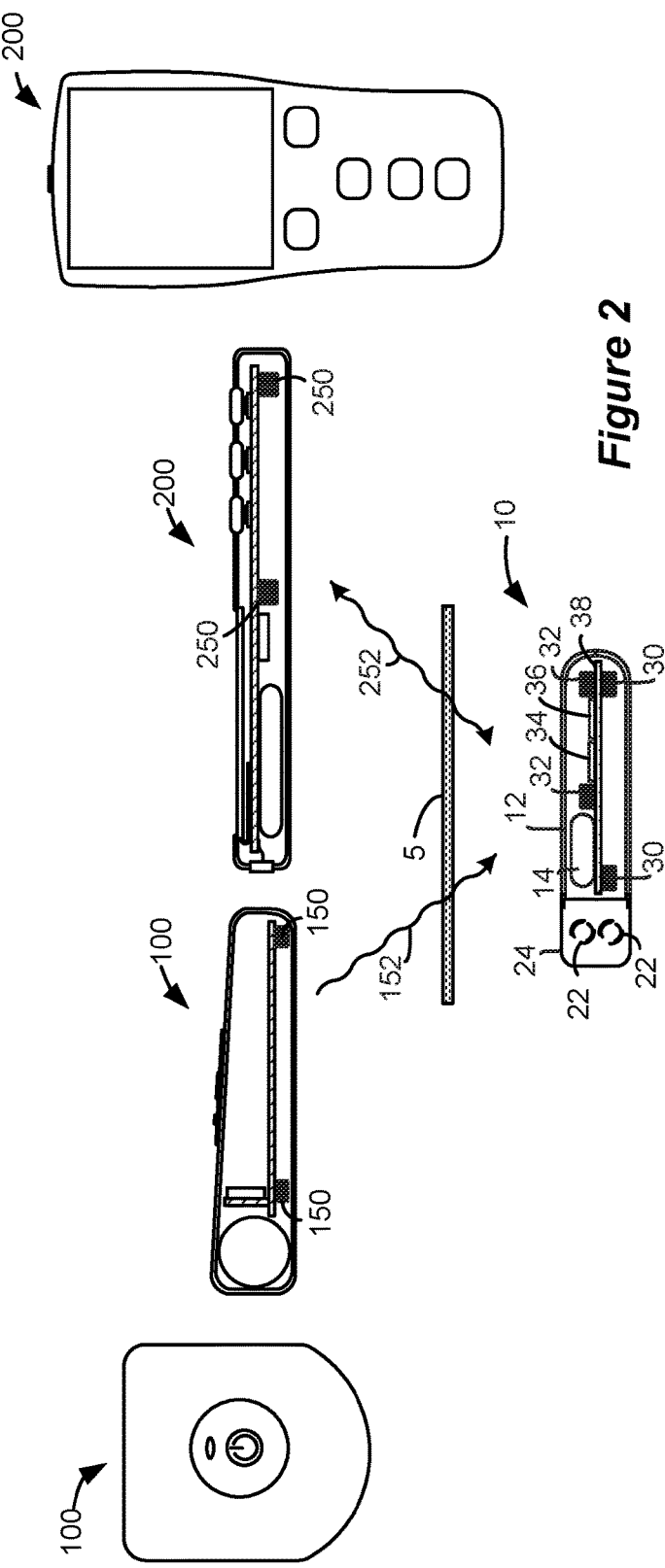
FIG. 2 shows a cross section of the IMD of FIG. 1 as implanted in a patient, as well as external devices that support the IMD, including an external charger and external controller.

FIG. 4 illustrates a modified charger 100' that includes circuitry that enables the charger 100' to produce a static electromagnetic field that mimics the magnet 300. The modified external charger 100', just like the charger 100, is primarily used to charge (or recharge) the IMD 10's battery 14. A battery 156 in the external charger 100' provides operational power for the charger 100 and energy for the production of the magnetic charging field 152. Specifically, and as described above with respect to FIG. 2, the external charger 100 includes charging circuitry 164, which contains drive circuitry 160 that energizes the coil 150 with a non-modulated alternating current to create the magnetic charging field 152. The magnetic field 152 induces a current in the charging coil 30 within the IMD 10, which current is rectified (70) to DC levels, and used to recharge the battery 14, perhaps via a charging and battery protection circuit 72 as shown.

The IMD 10 can also communicate data back to the external charger 100' using Load Shift Keying (LSK) modulation circuitry 74. LSK modulation circuitry 74 receives data to be transmitted back to the external charger 100' from the IMD 10's microcontroller 34, and then uses that data to modulate the impedance of the charging coil 30. The coil 30's impedance is modulated via control of transistor 76, which shorts both ends of the coil 30 to ground. Impedance modulation could alternatively be accomplished by shorting both ends of the coil 30 together. The change in impedance is reflected back to coil 150 in the external charger 100', which interprets the reflection at LSK demodulation circuitry 162 to recover the transmitted data. This means of transmitting data from the IMD 10 to the external charger 100' is useful to communicate data relevant to charging of the battery 14, such as the battery level, whether charging is complete and the external charger can cease, and other pertinent charging variables. However, because LSK works on a principle of reflection, such data can only be communicated from the IMD 10 to the external charger 100' during periods in which the external charger 100' is active and is producing a magnetic charging field 152.

The charger 100' is modified in the sense that drive circuitry 160 can operate in a magnet mode of operation in addition to its normal charge mode of operation. The magnet mode may be initiated by the user such as via button 140, the status of which is monitored by the microcontroller 158. Because the charger 100' may have a relatively simple interface, the button 140 may also be used for other functions such as initiating charging. For example, a single press of the button 140 may initiate the charge mode while a double press of the button 140 may initiate the magnet mode. In another embodiment, the button 140 may be separate from an input that is used to initiate charging. In any event, because the magnet mode of operation will cause the emergency shutdown of the IMD 10 when the charger 100' is brought into its vicinity, the charger 100' may be designed to prevent inadvertent initiation of the magnet mode. The desired mode of operation (charge, magnet, or off) is communicated from the microcontroller 158 to the charging circuitry 164, and the charging circuitry 164 is differently configured based on the selected mode. The charger 100' may be programmed with instructions that are embodied on a non-transitory computer-readable medium and that are executable by the microcontroller 158 or other control circuitry to cause the charging circuitry 164 to operate in the different modes of operation.

FIG. 5 illustrates an example of the charging circuitry 164 of the charger 100'. In the illustrated example, the charging circuitry 164 includes a well-known H-bridge configuration, including two switches (P-channel transistors) coupled to the output of a voltage generator 130, and two switches (N-channel transistors) coupled to a reference potential such as ground (GND). The transistors are controlled by a drive signal D (and its logical complement D*), which is generated by a signal generator 120 to control a conductive path through the coil 150. The voltage generator 130 (e.g., a switching regulator, etc.) receives the battery voltage Vbat (or another voltage derived from Vbat), and generates a constant voltage at its output. The voltage generator 130 and the signal generator 120 receive a magnet/charge signal that is indicative of the desired mode of operation.

In the charge mode of operation, the voltage generator 130 produces a voltage Vcharge at its output and the signal generator 120 generates a signal Dcharge. The voltage Vcharge, in one example, may have a magnitude of approximately 3.0 volts. The signal Dcharge is a square wave signal that drives transistors Q1, Q2, Q3, and Q4 and causes the supply voltage Vcharge and ground to alternate across the LC circuit 168, which comprises the coil 150 and a tuning capacitor 166, at frequency f, thus producing the magnetic charging field 152 at this frequency. Current flows along the path Ia when the value of D is '0' and along the path Ib when the value of D is '1', thus alternating its direction through the LC circuit 168 as the value of D alternates. As is well known, the duty cycle DC of the drive signal D can be adjusted (e.g., up to 50%) to adjust the average current through the LC circuit 168, thus increasing the power of the resulting magnetic field 152. Note that the magnetic field 152 that is generated in the charge mode of operation does not result in the emergency shutdown of the IMD 10. This can be because the strength of the magnetic field 152 is insufficient to be detected by the sensor 306, because the signal conditioning circuit 308 prevents the initiation of the emergency shutdown as a result of the alternating magnetic field 152 (i.e., requires a static magnetic field), or both.

In the magnet mode of operation, the voltage generator 130 produces a voltage Vmagnet at its output and the signal generator 120 generates a signal Dmagnet. The signal Dmagnet is held at a constant value of either '0' or '1' for an extended period of time to produce a direct current through the LC circuit 168 and a static magnetic field 152. Because the capacitor 166 will not pass a direct current, a switch 167 is provided to bypass the capacitor 166 to allow the LC circuit 168A to function in the magnet mode of operation. The static magnetic field 152 mimics the field generated by the magnet 300 and therefore the charger 100' can initiate a shutdown of the IMD 10 when the charger 100' is placed in the magnet mode of operation and is brought into proximity of the IMD 10. The current through the LC circuit 168 in the magnet mode (either Ia or Ib depending on the value of D) is given by I=Vmagnet/R, where R is the sum of the resistances of the P-channel transistor, the N-channel transistor, and the coil 150 along the current path between Vmagnet and ground. The strength of the static magnetic field that is produced is equal to the product of the current through the coil 150 (Ia or Ib) and the number of turns of the coil 150. Given the known number of turns of the coil 150 and resistance of components in the current paths, the voltage Vmagnet can be selected to produce a current that results in the desired magnetic field strength. The magnetic field strength may be selected to match the strength of the magnetic field generated by the magnet 300 or it may be selected at any other desired strength that is sufficient to be recognized by the sensor 306. In one example, the magnitude of Vmagnet may be approximately 3.0 volts to produce a current (Ia or Ib) having a magnitude of approximately 3.0 amps through the coil 150, which may have 100 turns, thus resulting in a static magnetic field 152 having a magnitude of approximately 2 millitesla in the center of the coil at a distance of 3 cm. Note that the signal Dmagnet is selectable to control the polarity of the current through the coil 150 (i.e., either Ia or Ib) such that the direction of the magnetic field can be selected should such directional selectivity be meaningful for a given sensor 306. Although not illustrated, the magnet/charge mode of operation signal may additionally be utilized to decouple the LSK demodulation circuitry 162 from the coil 150 in the magnet mode of operation.

Figure 6A:
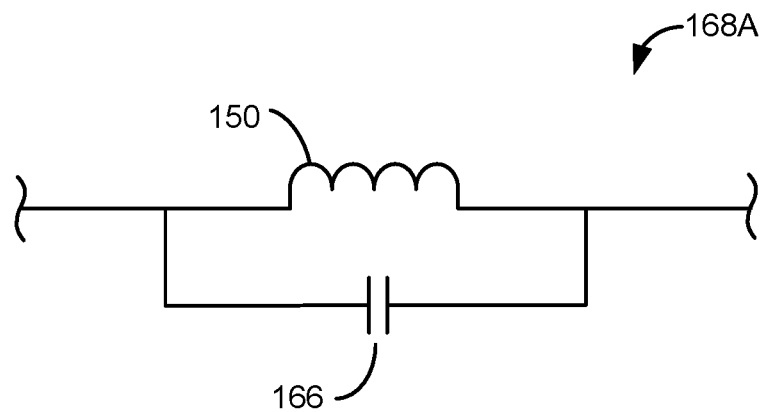
FIGS. 6A-6C show example LC circuits in the modified external charger in accordance with aspects of the disclosure.

While FIG. 5 illustrates a series resonance LC circuit 168, it will be understood that the coil 150 and capacitor 166 may alternatively be connected in parallel as shown in the parallel resonance LC circuit 168A in FIG. 6A, which circuit 168A may replace the series resonance LC circuit 168 in FIG. 5. Note that switch 167 is not needed in the parallel resonance LC circuit 168A.

Figure 6B:
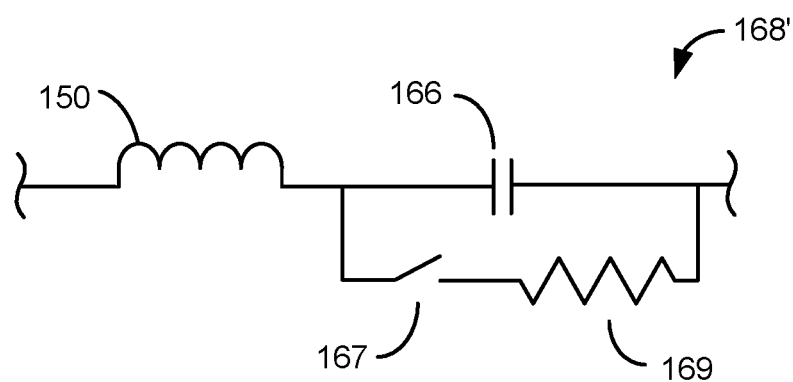
Figure 6C:
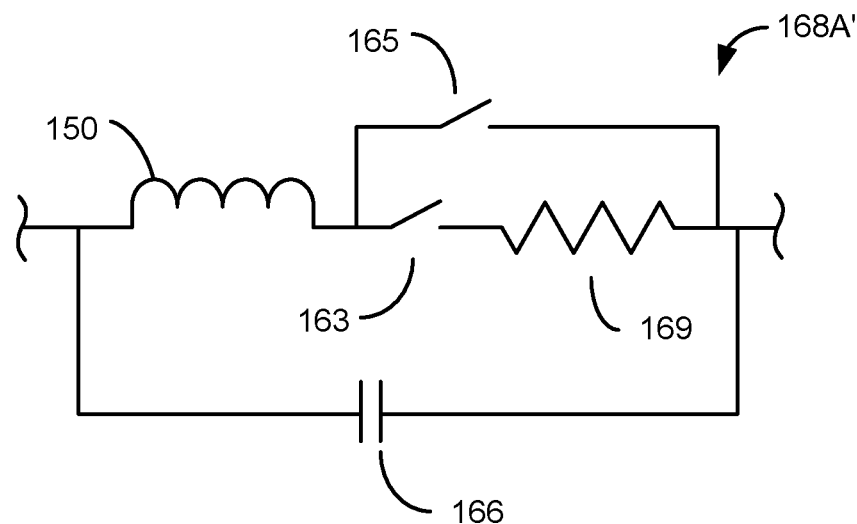

The charging circuitry 164 can also be modified such that the voltage supplied to the H-bridge configuration is the same regardless of the mode of operation, thus eliminating the requirement for the voltage generator 130 to receive the mode of operation signal. FIGS. 6B and 6C show modified LC circuits 168' and 168A' that can be substituted for circuits 168 and 168A, respectively, to accomplish such a constant-voltage configuration. In lieu of adjusting the voltage to Vmagnet, a resistor 169 is switched into series with the coil 150 in the magnet mode of operation. In circuit 168', which is a series resonance circuit, the resistor 169 is switched into series with the coil 150 by closing the switch 167 in the magnet mode and is removed from the circuit 168' by opening the switch 167 in the charge mode. In circuit 168A', which is a parallel resonance circuit, the resistor 169 is switched into series with the coil 150 by closing the switch 163 and opening the switch 165 in the magnet mode and is bypassed by closing the switch 165 and opening switch 163 in the charge mode. The magnitude of the resistance provided by the resistor 169 is selected such that the desired current through the coil 150 is obtained for the voltage Vcharge that is supplied to the H-bridge configuration in both the charge and magnet modes of operation.

Although not shown, the switches 163, 165, and 167 are toggled based on the mode of operation signal. The switches 163, 165, and 167 may each be implemented as field-effect transistors (FETs), an electro-mechanical relay, a solid-state relay, or any other arrangement that is capable of passing current in either direction in the 'ON' state and fully blocking current in either direction in the 'OFF' state.

Figure 7:
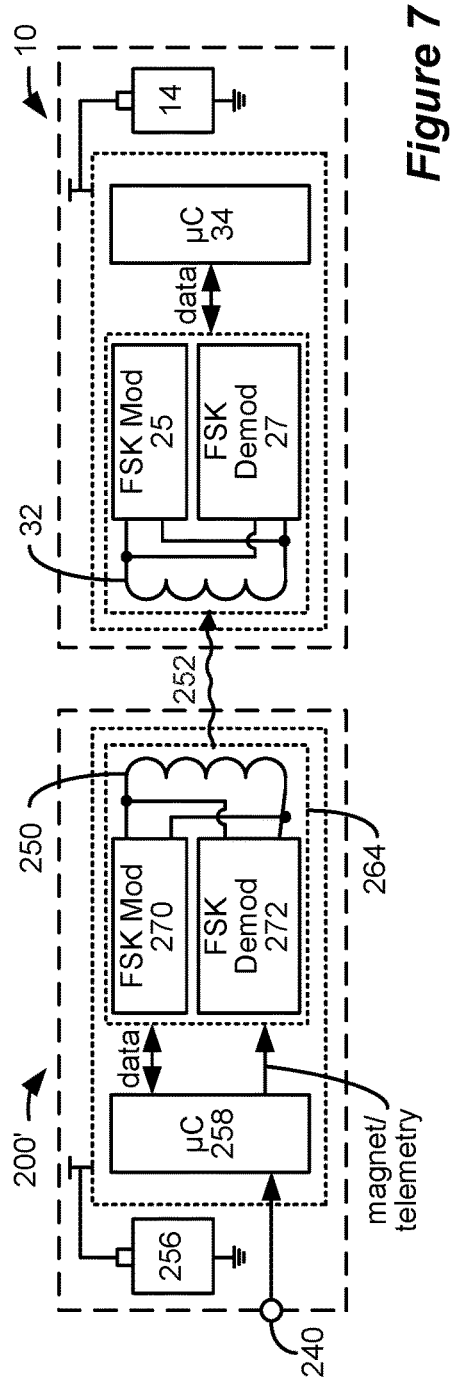
FIG. 7 is a block diagram showing circuitry in a modified external controller and an IMD in accordance with aspects of the disclosure.

FIG. 7 illustrates a modified controller 200' that includes coil drive circuitry 264 that enables the controller 200' to wirelessly transfer data with the IMD 10. Wireless data transfer between the external controller 200' and the IMD 10 occurs in a telemetry mode of operation over link 252 via magnetic inductive coupling between coils 250 and 32, either of which can act as the transmitter or the receiver to enable two-way communication between the two devices. When a series of digital data bits is to be sent from the external controller 200' to the IMD 10, control circuitry 258 (e.g., a microcontroller) provides these bits in sequence to a modulator 270. Modulator 270 energizes coil 250 with an alternating current (AC) whose frequency is modulated in accordance with the state of the data bit currently being transferred in accordance with a Frequency Shift Keying (FSK) protocol. For example, the coil 250 may nominally be tuned to resonate at 125 kHz in accordance with the inductance of the coil 250 and a tuning capacitor 266 (FIG. 8), with the data states '0' and '1' altering this center frequency to $f_0$=121 kHz and $f_1$=129 kHz respectively. The frequency-modulated current through the coil 250 in turn generates a frequency-modulated magnetic field comprising link 252, which in turn induces a frequency-modulated current in the IMD's telemetry coil 32. This received signal is demodulated 27 back into the series of digital data bits, and sent to control circuitry 34 (e.g., a microcontroller) in the IMD 10 for interpretation. Data telemetry in the opposite direction from IMD 10 to external controller 200' occurs similarly via modulator 25 and demodulator 272.

The controller 200' is modified in the sense that drive circuitry 264 can operate in a magnet mode of operation in addition to its normal telemetry mode of operation. The magnet mode may be initiated by the user such as via button 240, the status of which is monitored by the microcontroller 258. Unlike the charger 100', the controller 200' may have a more complex interface, and the button 240 may be a physical button or an option selected via an interface provided on a screen of the controller 200'. Just as with the charger 100', because the magnet mode of operation will cause the emergency shutdown of the IMD 10 when the controller 200' is brought into its vicinity, the controller 200' may be designed to prevent inadvertent initiation of the magnet mode. The desired mode of operation (telemetry, magnet, or off) is communicated from the microcontroller 258 to the drive circuitry 264, and the drive circuitry 264 is differently configured based on the selected mode. The controller 200' may be programmed with instructions that are embodied on a non-transitory computer-readable medium and that are executable by the microcontroller 258 or other control circuitry to cause the drive circuitry 264 to operate in the different modes of operation.

Figure 8:
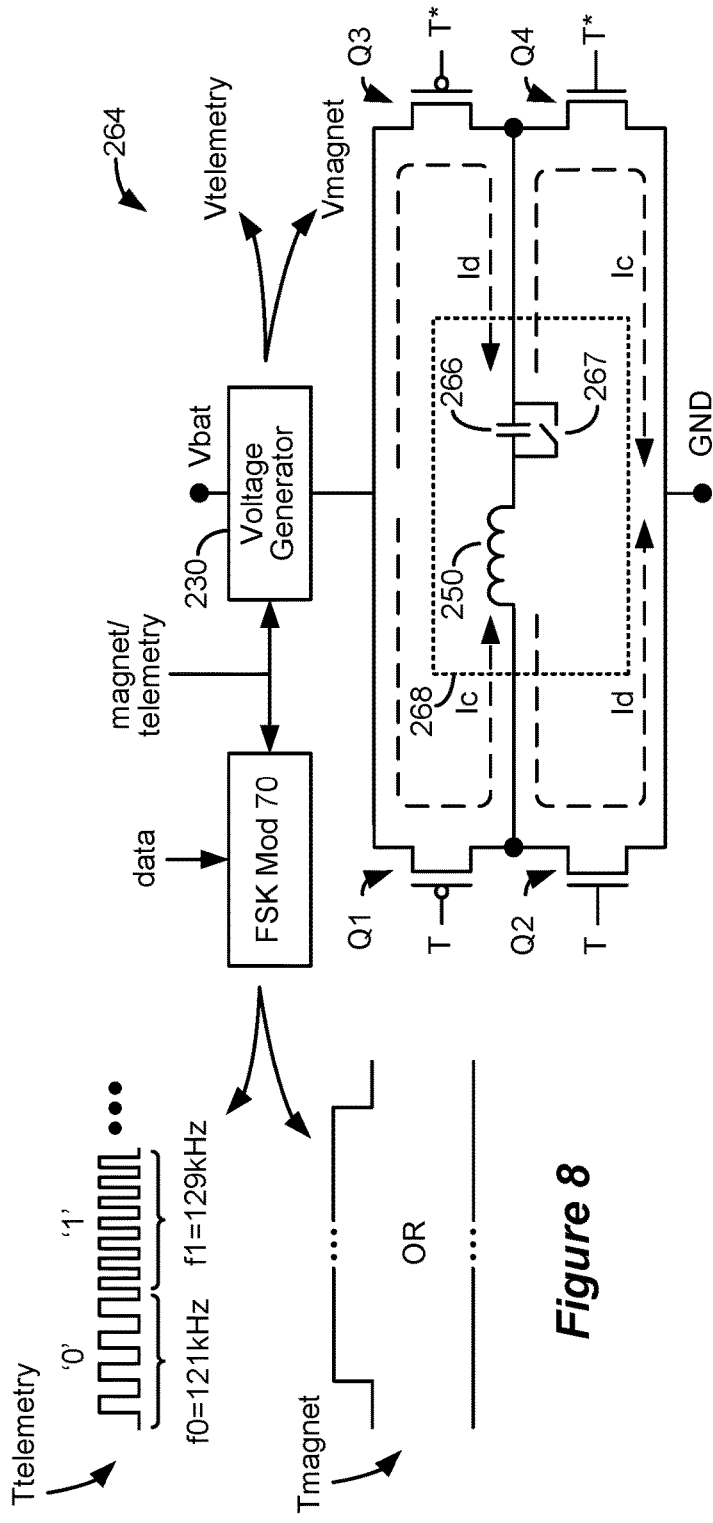
FIG. 8 shows components of example coil drive circuitry in the modified external controller in accordance with aspects of the disclosure.

FIG. 8 illustrates an example of the coil drive circuitry 264 of the controller 200'. In the illustrated example, the coil drive circuitry 264 largely mirrors the H-bridge configuration of the charging circuitry 164 of the charger 100'. The transistors are controlled by a drive signal T (and its logical complement T*), which is generated by FSK modulation circuitry 270 to control a conductive path through the coil 250. The voltage generator 230 (e.g., a switching regulator, etc.) receives the battery voltage Vbat (or another voltage derived from Vbat), and generates a constant voltage at its output. The voltage generator 230 and the FSK modulation circuitry 270 receive a magnet/telemetry signal that is indicative of the desired mode of operation.

In the telemetry mode of operation, the voltage generator 230 produces a voltage Vtelemetry at its output and the FSK modulation circuitry 270 generates a signal Ttelemetry. The voltage Vtelemetry, in one example, may have a magnitude of approximately 3.0 volts. The signal Ttelemetry is a square wave signal that drives transistors Q1, Q2, Q3, and Q4 (note that these transistors differ from the transistors in the charger 100' that share the same label) with a frequency that varies in accordance with the data bit that is being transmitted. In the illustrated example, the Ttelemetry signal is modulated at 121 kHz to represent a '0' bit and at 129 kHz to represent a '1' bit. Current flows along the path Ic when the value of T is '0' and along the path Id when the value of T is '1', which causes the supply voltage Vtelemetry and ground to alternate across the LC circuit 268 at the selected frequency f0 or f1, thus producing the alternating magnetic field 252 at the same frequency. Note that the magnetic field 252 that is generated in the telemetry mode of operation does not result in the emergency shutdown of the IMD 10. This can be because the strength of the magnetic field 252 is insufficient to be detected by the sensor 306, because the signal conditioning circuit 308 prevents the initiation of the emergency shutdown as a result of the alternating magnetic field 252 (i.e., requires a static magnetic field), or both.

In the magnet mode of operation, the voltage generator 230 produces a voltage Vmagnet (note that the voltage Vmagnet produced by the voltage generator 230 may differ from the voltage Vmagnet produced by the voltage generator 130) at its output and the FSK modulation circuitry 270 generates a signal Tmagnet. The signal Tmagnet functions in the same way as Dmagnet (i.e., held at a constant value of either '0' or '1' for an extended period of time) to produce a direct current through the LC circuit 268 and a static magnetic field 252. The static magnetic field 252 mimics the field generated by the magnet 300 and therefore the controller 200' can initiate a shutdown of the IMD 10 when the controller 200' is placed in the magnet mode of operation and is brought into proximity of the IMD 10. The current through the LC circuit 268 in the magnet mode (either Ic or Id depending on the value of T) is given by I=Vmagnet/R, where R is the sum of the resistances of the P-channel transistor, the N-channel transistor, and the coil 250 along the current path between Vmagnet and ground. The strength of the static magnetic field that is produced is equal to the product of the current through the coil 250 (Ic or Id) and the number of turns of the coil 250. Given the known number of turns of the coil 250 and resistance of components in the current paths, the voltage Vmagnet can be selected to produce a current that results in the desired magnetic field strength. The magnetic field strength may be selected to match the strength of the magnetic field generated by the magnet 300 or it may be selected at any other desired strength that is sufficient to be recognized by the sensor 306. In one example, the magnitude of Vmagnet may be approximately 3.0 volts to produce a current (Ic or Id) having a magnitude of 3.0 amps through the coil 250, which may have 100 turns, thus resulting in a static magnetic field 252 having a magnitude of approximately 2 millitesla in the center of the coil at a distance of 3 cm. Note that the signal Tmagnet is selectable to control the polarity of the current through the coil 250 (i.e., either Ic or Id) such that the direction of the magnetic field can be selected should such directional selectivity be meaningful for a given sensor 306. While a series resonance LC circuit 268 in which the voltage is varied depending on the mode of operation is illustrated in FIG. 8, it will be understood that the circuit 268 can also be modified in the same way as described above with respect to FIGS. 6A-6C. Although not illustrated, the magnet/telemetry mode of operation signal may additionally be utilized to decouple the FSK demodulation circuitry 272 from the coil 250 in the magnet mode of operation.

Although the above external devices utilize a coil that is primarily used for a different purpose (i.e., the charge coil 150 in charger 100' and telemetry coil 250 in controller 200') to additionally create a static magnetic field to initiate a shutdown of the IMD 10, these devices could alternatively include a dedicated coil for generating the static magnetic field. For example, the charger 100' could include a dedicated coil in addition to the charge coil 150 that would only be used in the magnet mode of operation to generate the static magnetic field. Similarly, the controller 200' could include a dedicated coil in addition to the telemetry coil 250 (or other type of antenna) that would only be used to generate the static magnetic field. This would allow the charge coil 150 or telemetry coil 250 (or other type of antenna) to perform only their respective charging and telemetry functions in the normal mode of operation and to be simply decoupled from their respective drive circuits in the magnet mode of operation. The dedicated coil in each of the devices may be connected to a supply voltage by a switch that is closed in the magnet mode to cause a direct current to flow through the coil to generate a static magnetic field of the desired strength. Alternatively, the dedicated coil may be connected in an H-bridge arrangement such as those described above to enable the polarity of the current through the dedicated coil to be selected to control the direction of the resulting magnetic field.

While H-bridge configurations have been illustrated as examples of circuitry used to drive a coil (e.g., charge coil 150 and telemetry coil 250), it will be understood that different types of circuits may be employed to drive a coil. Moreover, while the application has focused on the generation of a static electromagnetic field for the purpose of inducing an emergency shutdown of an IMD, the static electromagnetic field may be used to induce other status changes in an 1 MB. For example, a static electromagnetic field may replace a magnet for the purpose of ensuring security such as when establishing a communications link between the IMD and a new external device such as a mobile phone. Other types of 1 MB status changes may also be induced via an electromagnetic field generated by an external device.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. A system, comprising:
an implantable medical device; and
an external device, comprising:
a coil; and
circuitry that is configured to produce a direct current through the coil in a first mode of operation to generate a static magnetic field to change a status of the implantable medical device.

2. The system of claim 1, wherein the implantable medical device comprises a magnet sensor to detect the static magnetic field.

3. The system of claim 2, wherein the magnet sensor is a reed switch.

4. The system of claim 2, wherein the magnet sensor is a Hall effect sensor.

5. The system of claim 2, wherein the implantable medical device further comprises a signal conditioning circuit that receives a signal from the magnet sensor.

6. The system of claim 2, wherein the implantable medical device further comprises circuitry that is configured to disconnect one or more components in the implantable medical device from a battery in the implantable medical device when the magnet sensor detects the static magnetic field.

7. The system of claim 1, wherein the external device is an external charger.

8. The system of claim 7, wherein the circuitry is configured to produce an alternating current through the coil in a second mode of operation.

9. The system of claim 8, wherein the alternating current produces an alternating magnetic field to charge a battery in the implantable medical device.

10. The system of claim 1, wherein the external device is an external controller.

11. The system of claim 10, wherein the circuitry is configured to produce an alternating current through the coil in a second mode of operation.

12. The system of claim 11, wherein the circuitry is configured to communicate data to the implantable medical device using a frequency of the alternating current.

13. The system of claim 1, wherein the circuitry comprises a signal generator that generates a signal to control a conductive path through the coil.

14. The system of claim 13, wherein the circuitry comprises an H-bridge and wherein the signal controls a plurality of switches in the H-bridge.

15. The system of claim 13, wherein the signal is a constant signal in the first mode of operation.

16. The system of claim 13, wherein the signal is a square wave signal in a second mode of operation, and wherein the square wave signal produces an alternating current through the coil.

17. The system of claim 16, wherein the circuitry is configured to adjust a duty cycle of the square wave signal to control a strength of an alternating magnetic field that is produced by the alternating current through the coil.

18. A method for operating an external device to control an implantable medical device, wherein the external device comprises a coil, the method comprising:
producing a direct current through the coil in a first mode of operation of the external device to generate a static magnetic field to change a status of the implantable medical device.

19. The method of claim 18, further comprising:
producing an alternating current through the coil in a second mode of operation of the external device to generate an alternating magnetic field.

20. The method of claim 19, wherein the alternating magnetic field is used to charge a battery in the implantable medical device, or to communicate data to the implantable medical device.

* * * * *